United States Patent
Nakamura et al.

(10) Patent No.: US 6,527,708 B1
(45) Date of Patent: Mar. 4, 2003

(54) ENDOSCOPE SYSTEM

(75) Inventors: Tetsuya Nakamura, Saitama-ken (JP); Tetsuya Utsui, Saitama-ken (JP); Ryo Ozawa, Tokyo (JP); Shinsuke Okada, Saitama-ken (JP); Masaru Eguchi, Tokyo (JP); Koichi Furusawa, Tokyo (JP)

(73) Assignee: Pentax Corporation, Tokyo (JP)

( * ) Notice: Subject to any disclaimer, the term of this patent is extended or adjusted under 35 U.S.C. 154(b) by 102 days.

(21) Appl. No.: 09/605,852

(22) Filed: Jun. 29, 2000

(30) Foreign Application Priority Data

Jul. 2, 1999 (JP) .......................... 11-189110
Jul. 2, 1999 (JP) .......................... 11-189111

(51) Int. Cl.⁷ .............................. A61B 1/04; A61B 1/06
(52) U.S. Cl. ................... 600/160; 600/109; 600/178
(58) Field of Search ................ 600/160, 109, 600/118, 173, 178, 181–182

(56) References Cited

U.S. PATENT DOCUMENTS

| 5,321,501 A | | 6/1994 | Swanson et al. |
| 5,459,570 A | * | 10/1995 | Swanson ..................... 356/345 |
| 5,471,988 A | * | 12/1995 | Fujio et al. .................. 600/439 |
| 6,069,698 A | | 5/2000 | Ozawa et al. |
| 6,134,003 A | * | 10/2000 | Tearney ...................... 356/345 |
| 6,293,911 B1 | * | 9/2001 | Imaizumi ..................... 600/160 |
| 6,191,852 B1 | * | 2/2002 | Swanson ...................... 356/450 |

FOREIGN PATENT DOCUMENTS

| JP | 6-154228 | 6/1994 |
| JP | 11-56751 | 3/1999 |
| JP | 11-56752 | 3/1999 |

OTHER PUBLICATIONS

A.M. Sergeev et al., *In vivo endoscopic OCT image of precancer and cancer states of human mucosa*, Optics Express, vol. 1, No. 13, Dec. 22, 1997, pp. 432–440.

G.J. Tearney et al., *In Vivo Endoscopic Optical Biopsy with Optical Coherence Tomography*, Science, vol. 276, Jun. 27, 1997, pp. 2037–2039.

* cited by examiner

*Primary Examiner*—Denise M. Pothier
(74) *Attorney, Agent, or Firm*—Greenblum & Bernstein, P.L.C.

(57) ABSTRACT

An endoscope system capable of obtaining a normal light image and/or fluorescent light image is further provided with an a low-coherent light source arranged on a proximal end side of one of first and second light guides. A scanning unit is provided to cause the low-coherent light beam emerged from a tip of the first light guide to scan on the object. The low-coherent light reflected by the object is directed to the first light guide by the scanning unit as detecting light. A mirror is provided to reflect the low-coherent light beam emerged from a tip of the second light guide. A detector is arranged on a proximal end side of the other of the first and second light guides to detect interference fringe pattern generated by interference between the detecting light and the reference light. By changing a length of an optical path, via the first light guide, from the coupler to the object relative to a length, via the second light guide, of an optical path from the coupler to the mirror, a tomogram of the object can be captured.

10 Claims, 4 Drawing Sheets

ENDOSCOPE SYSTEM

BACKGROUND OF THE INVENTION

The present invention relates to an endoscope system capable of capturing in vivo normal light images and fluorescent light images of a surface of an object, and OCT (optical coherence tomography) images of the object.

Endoscope systems used for observing inside a body cavity of a patient have been conventionally known. An example of conventional endoscope systems includes an endoscope to be inserted in the body cavity of the patient, and an external device connected to the endoscope. The external device includes a light source and an image processor.

The endoscope includes an illuminating optical system, which is connected to:

the light source of the external device, the illuminating optical system emitting light toward an object to be observed for illuminating the same;

an objective optical system for forming an object image; and a CCD (Charge Coupled Device), which is arranged at an image plane of the objective optical system and is connected to the image processor of the external device.

At the distal end of the endoscope, an instrument outlet, from which various treatment instruments such as a forceps are to be protruded, is defined.

An operator of the endoscope system inserts the endoscope inside the body cavity of the patient, and illuminates paries of the cavity with the light emitted through the illuminating optical system. An image of the paries is formed by an objective optical system. The CCD converts the thus formed image (optical image) into an electrical signal (i.e., electrical image) and transmits the signal to the image processor included in the external device.

The external device processes the received image signal representing the image of the paries of the body cavity, and displays the image on a monitor. Thus, the operator is capable of observing the image of the paries of the body cavity displayed on the monitor.

If the operator determines that there is a portion which might be cancered or tumorous, the operator collects the biotissues at the portion using forceps or a biopsy needle protruded from the instrument outlet. The thus obtained biotissues are subjected to a pathological examination, based on the results of which a diagnosis is made.

In the conventional endoscope as described above, the displayed image shows only the surface of the paries of the body cavity. In order to know the condition of the tissues beneath the surface of the paries, biopsy is required. In particular, in order to detect cancer in its earliest form or relatively small tumors, the biopsy is indispensable. However, pathologic investigation of the biotissues obtained by the biopsy generally takes time, and therefore, the diagnosis also takes time.

Further, in view of the burden to the patient, the biopsy is to be done for only a limited portion by a limited amount of time. However, there is a possibility that portions other than those identified by the operator are diseased. Thus, unless the biopsy is done with respect to the diseased area, the accurate diagnosis cannot be expected.

Incidentally, a method for obtaining tomogram of biotissues utilizing a combination of a low-coherent light source such as a superluminescent diode (SLD) and a Michelson interferometer has been developed. Such a method is known as an OCT (Optical Coherent Tomography) system, an example of which is described in U.S. Pat. No. 5,321,501, the teachings of which are incorporated herein by reference.

For one solution of the afore-mentioned problem, an imaging system including a probe of the OCT has been known. Such a system is described in "In vivo endoscopic OCT imaging of precancer and cancer states of human mucosa", by A. M. Sergeev et al., Dec. 22, 1997, vol. 1, No. 13 of OPTICS EXPRESS pp. 432–440, teaching of which is incorporated herein by reference.

In the above OCT system, however, a tomogram for a relatively wide area cannot be obtained at one time. Therefore, an operator of the system designates a portion, which might be diseased, and the OCT imaging is performed with respect to the designated portion. If the OCT system is incorporated in an endoscope system, the operator inserts the endoscope in the body cavity for normal observation, identifies a portion which might be diseased, and then performs the OCT imaging with respect to the identified portion.

FIG. 6 shows an example of a conventional OCT imaging system for an endoscope. In FIG. 6, a distal end portion 7 of the endoscope is shown. The distal end portion 7 has a substantially cylindrical shape, and on the tip end surface, an illumination window 71, an observation window 72 and an instrument outlet opening 73 are formed. Inside the endoscope, although not shown, an illuminating optical system for directing a visible light beam is provided. Further, the endoscope is provided with an objective optical system (not shown) for receiving light from an object (e.g., a surface of the paries which is considered to be diseased) and forming an object image on an image receiving surface of a CCD (Charge Coupled Device), not shown.

The illumination optical system emits visible light through the illumination window 71 toward the object. The light reflected by the object enters the objective lens system through the observation window 72. Then, an image of the object is formed on the image receiving surface of the CCD. The CCD then outputs an image signal, which is processed and displayed on a monitor 8 as a normal image.

Separate from the endoscope, an OCT apparatus having the SLD and a Michelson interferometer is provided. The interferometer Is provided with a measuring optical system and a reference optical system. The measuring optical system includes a fiber probe 9, which is inserted through the endoscope, and the tip thereof is protruded from the instrument outlet 73 of the distal end portion 7 of the endoscope. The OCT apparatus is also connected to the monitor 8, and an OCT image of a portion facing the tip end of the fiber probe 9 is displayed on the monitor 8.

When in use, the operator inserts the endoscope inside the body cavity of the patient, and observes the normal image of the paries. If a portion which might be diseased is found, the operator makes the fiber probe 9 protrude from the instrument outlet 73 to confront with the portion in question. Then, the OCT apparatus is operated to capture a tomogram of the portion in question, and displays the same on the monitor 8.

The monitor 8 is capable of selectively displaying the normal image and the OCT image in accordance with operation of switches and/or keyboard 6. In FIG. 6, the monitor 8 displaying the normal image and the monitor 8 displaying the OCT image are drawn in order to show both conditions. Actually, however, the endoscope system is provided with only one monitor 8, and one of the normal image and the OCT image is displayed on the monitor 8. The operator makes diagnosis in accordance with thus displayed images.

According to the conventional endoscope system described above, the fiber probe 9 of the OCT apparatus protrudes from the instrument outlet 73. The fiber probe 9 is located within a field of view of the objective optical system. Therefore, in the normal image displayed on the monitor 8, the fiber probe 9 appears and forms a dead angle. The dead angle disturbs the observation of the normal image, which prevents the operator from recognizing positional relationship between the normal image and the OCT image.

In order to avoid such a problem, the objective optical system for the normal image and the tip of the measuring optical system of the OCT apparatus can be Integrated to a single optical system. In such a case, however, it becomes generally necessary to split optical paths of the normal image and the OCT image utilizing a half mirror, a dichroic mirror and the like. In such a configuration, the light amount is decreased when the light incident from the object is split, which deteriorates quality of the images.

SUMMARY OF THE INVENTION

In view of the above problems, it is an object of the present invention to provide an improved endoscope system that enables diagnosis accurately within a relatively short period of time.

Another object of the present invention is to provide an improved endoscope system which is capable of capturing images of relatively high quality, and is also capable of obtaining the OCT image.

For an object, according to the present invention, there is provided an endoscope system, which is provided with an illuminating optical system that emits at least one of visible light and excitation light for illuminating an object to be observed, the excitation light causing biotissues to fluoresce, an objective optical system that converges light from the object to form an optical image of the object, an image capturing system that captures the optical image formed by the objective optical system, a first light guide, a second light guide, a coupler, the first and second light guides being optically coupled by the coupler, a low-coherent light source arranged on a proximal end side of one of the first and second light guides, a low-coherent light beam emitted by the low-coherent light source being incident on the one of the first and second light guides, a scanning unit that causes the low-coherent light beam emerged from a tip of the first light guide to scan on the object, the low-coherent light reflected by the object being directed to the first light guide by the scanning unit as detecting light, a mirror that reflects the low-coherent light beam emerged from a tip of the second light guide so as to impinges on the tip of the second light guide as reference light, an optical path length adjusting system that changes a length of an optical path from the coupler to the object via the first light guide relative to a length of an optical path from the coupler to the mirror via the second light guide, a detector arranged on a proximal end side of the other of the first and second light guides, the detector detecting interference fringe generated by interference between the detecting light and the reference light and outputs an electrical signal, and a signal processing system that captures a tomogram of the object based on the signal that is output by the detector when the optical path length adjusting system and the scanning unit operate.

As above, the OCT image can be observed by monitoring the normal light image or the fluorescent light image. Therefore, diagnosis can be accurately performed within a relatively short period of time.

Optionally, the optical path length adjusting system may be configured to vary the length of the optical path from the coupler to the object via the first light guide relative to the length of the optical path from the coupler to the mirror via the second light guide by moving the mirror in a direction parallel to the central axis of the tip of the second light guide.

Further optionally, the signal processing system forms the tomogram of the object based on the signal output by the detector when the optical path length adjusting system periodically varies the length of the optical path from the coupler to the object via the first light guide relative to the length of the optical path from the coupler to the mirror via the second light guide, and when the scanning unit operates.

In particular, the signal processing system forms the tomogram when the optical path length adjusting system sequentially varies the length of the optical path from the coupler to the object via the first light guide relative to the length of the optical path from the coupler to the mirror via the second light guide for each scanning position.

Further optionally, the endoscope system may be provided with a visible light source, an excitation light source, a light source switching system that selectively introduces the light emitted by the visible light source and the excitation light source to the illuminating optical system. In this case, the objective optical system may form a normal light image of the object when the visible light is introduced to the illuminating, optical system, and the objective optical system may form a fluorescent light image of the object when the excitation light is introduced to the illuminating optical system.

Preferably, the low-coherent light source includes a superluminescent diode.

Still optionally, the endoscope system may include a display system for displaying an image of the surface of the object captured by the image capturing system and the tomogram of the object obtained by the signal processing system.

Further optionally, the scanning system emits the scanning beam through a scanning window, the scanning window being formed on an insertion tube of an endoscope of the endoscope system, the scanning window being located out of field of view of the objective optical system, the scanning window facing the object that is located within the field of view of the objective optical system.

With this structure, observation of the normal light image and/or fluorescent light image may not be disturbed by the tip portion of the insertion tube of the endoscope.

Optionally, the insertion tube includes a cylindrical portion and a flatter portion formed at a tip of the cylindrical portion, an inclined surface connecting side surfaces of the cylindrical portion and the flatter portion. Further, the illuminating optical system includes an illuminating lens that is fixed on the inclined surface and emits light toward the object. The objective optical system includes an objective lens that is fixed on the inclined surface and receives the light from the object, and the scanning window is provided on the side surface of the flatter portion.

Further optionally, the optical path length adjusting system may vary the length of the optical path from the coupler to the object via the first light guide relative to the length of the optical path from the coupler to the mirror via the second light guide by moving the mirror in a direction parallel to the central axis of the tip of the second light guide.

Further, the endoscope system may further be provided with a visible light source, an excitation light source, a light source switching system that selectively introduces the light emitted by the visible light source and the excitation light source to the illuminating optical system. In this case, the objective optical system forms a normal light image of the object when the visible light is introduced to the illuminating optical system, and the objective optical system forms a fluorescent light image of the object when the excitation light is introduced to the illuminating optical system.

Still optionally, the endoscope system may further be provided with a display system for displaying an image of the surface of the object captured by the image capturing system and the tomogram of the object obtained by the signal processing system.

DESCRIPTION OF THE ACCOMPANYING DRAWINGS

FIG. 1 is a block diagram of an endoscope system according to an embodiment of the invention;

FIG. 2 schematically shows a distal end portion of an endoscope;

FIG. 3 is a perspective view of the distal end portion of the endoscope;

FIG. 4 schematically shows optical paths of an OCT unit;

DESCRIPTION OF THE EMBODIMENT

An endoscope system according to an embodiment of the present invention will be described hereinafter with reference to the accompanying drawings.

Figure 1:
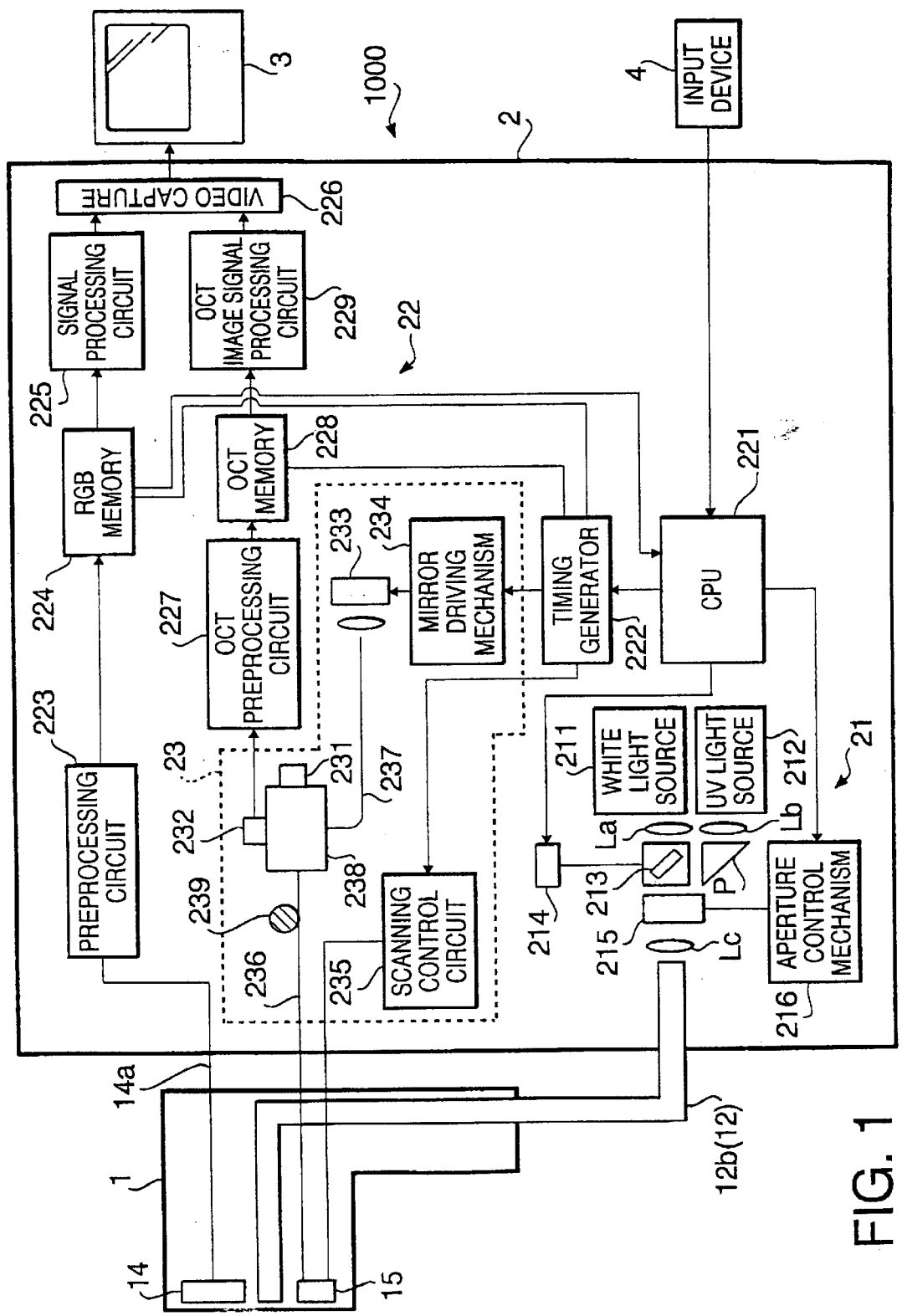

FIG. 1 is a block diagram of an endoscope system 1000 according to an embodiment of the invention. As shown in FIG. 1, the endoscope system 1000 includes an endoscope 1, an external device 2 connected to the endoscope 1, a monitor 3 connected to the external device 2, and an input device 4.

Figure 2:
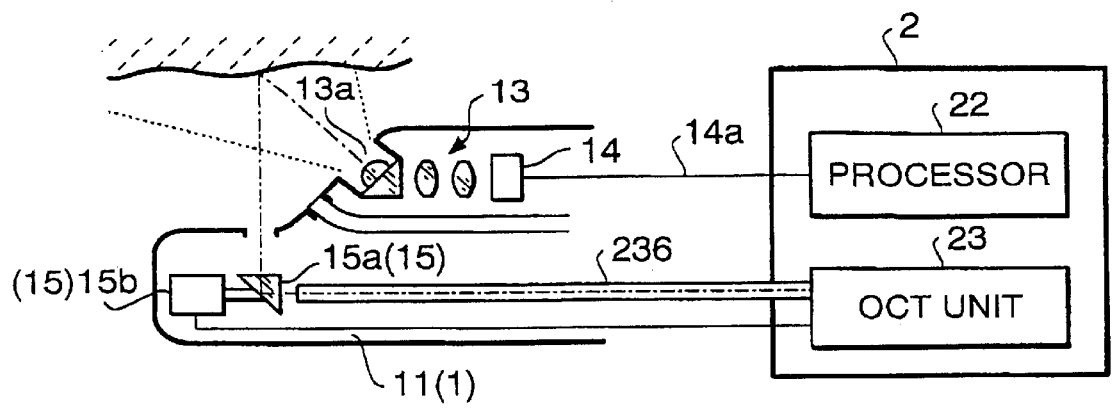
Figure 3:
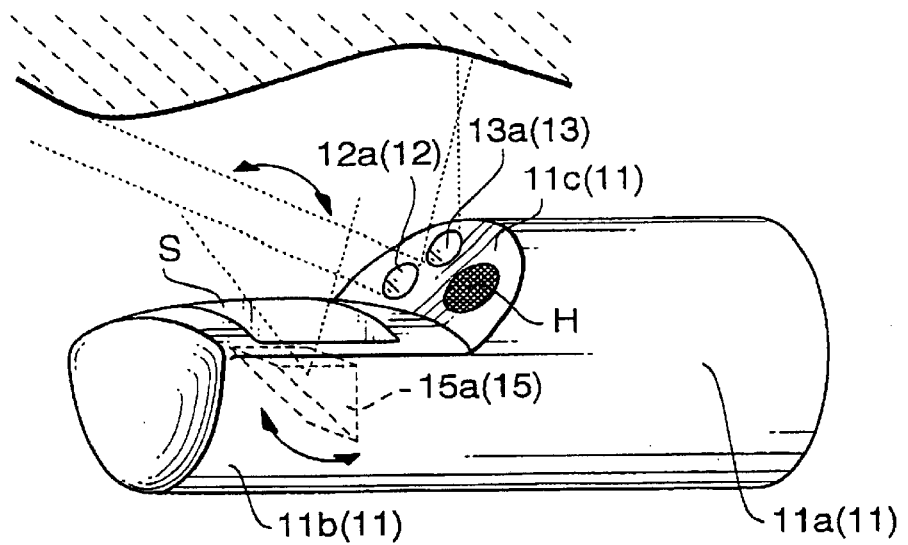

FIG. 2 schematically shows a distal end portion of an insertion tube 11 of the endoscope 1, and FIG. 3 is a perspective view of the distal end portion of an insertion tube 11 of the endoscope 1. It should be noted that, in FIGS. 2 and 3, only the distal end portion of the insertion tube 11 of the endoscope 1 is shown, the endoscope 1 is provided with an operation unit (not shown) provided with a plurality of switches at the proximal end portion thereof.

As shown in FIG. 3, the distal end portion of the insertion tube 11 is formed to have a substantially cylindrical part 11a extending from the proximal end portion of the endoscope 1, and a flatter part 11b having an elliptical cross section at the tip end of the cylindrical part 11a. The flatter part 11b is protruded in a direction parallel to the central axis of the cylindrical part 11a, and an inclined surface 11c connects side surfaces of the flatter part 11b and the cylindrical part 11a. The inclined surface 11c is formed with three through holes: one of which is used for an instrument outlet; and an illuminating lens 12a for emitting illuminating light and an objective lens 13a are fitted to the other two holes, respectively. On a side surface of the flatter part 11b, a scanning window S for an OCT scanning, which will be described later, is provided.

The insertion tube 11 accommodates an illumination optical system 12, an objective optical system 13, a CCD (Charge Coupled Device) 14, and an OCT scanning unit 15.

The illumination optical system 12 includes the afore-mentioned illuminating lens 12a and a light guide fiber bundle 12b (hereinafter, referred to as a light guide), which is inserted through the endoscope 1, a tip end of the light guide 12b facing the illuminating lens 12a, the proximal end being connected to the external device 2.

The objective optical system 13 includes a cut off filter for shielding ultraviolet light, a prism and a plurality of lenses as well as the objective lens 13a. The objective lens 13a converges the incident light on the image receiving surface of the CCD 14 to form an image of the object (e.g., an image of paries). In the embodiment, the CCD 14 is a color CCD which outputs a color (RGB) image signal to the external device 2 via a signal line 14a.

The OCT scanning unit 15 includes a scanning prism 15a, which faces a tip end of an optical fiber 236 (which will be described later) and deflect the light beam emitted by the optical fiber 236 toward the scanning window S, and a rotating unit 15b which reciprocally rotates the scanning prism 15a about the central axis of the optical fiber 236 within a predetermined angular range.

As afore-mentioned, the endoscope 1 constructed as above is connected to the external device 2. Hereinafter, the external device 2 will be described in detail.

As shown in FIG. 1, the external device 2 includes a light source unit 21, a processor 22, and an OCT unit 23.

The light source unit 21 includes a white light source 211 which emits white light (light having substantially all of visible wavelength components), and a UV light source 212 which emits excitation light. The excitation light is the light which causes biotissues to fluoresce when it is incident thereon. Generally, the excitation light is a ultraviolet light whose wavelength ranges from 350 nm through 380 nm, and the fluorescent light emitted by the biotissues, in response to the incidence of the excitation light, ranges from approximately 400 nm through 600 nm.

On the optical path of the white light emitted by the white light source 211, a collimating lens La, a switching mirror 213, an aperture stop 215 and a condenser lens Lc are arranged in this order.

The switching mirror 213 is connected to a light source switching mechanism 214. The light source switching mechanism 214 is capable of moving the switching mirror 213 at a first position where the switching mirror 213 is retracted from the optical path of the white light and allowing the white light to proceed along the optical path, and a second position where the switching mirror 213 is located on the optical path of the white light so as to prevent the white light from proceeding along a line extending along the light path on the downstream side of the switching mirror 213.

The aperture stop 215 is connected to the aperture control mechanism 216, which controls the aperture stop 215 to adjust the light amount (i.e., the aperture size).

The white light from the white light source 211 is collimated by the collimating lens La. If the switching mirror 213 is located at the first position, the white light proceeds toward the aperture stop 215. The white light, whose light amount is adjusted by the aperture stop 215, is converged, by the condenser lens Lc, on the proximal end surface of the light guide 12b.

On an optical path of the excitation light emitted by the UV light source 212, a collimating lens Lb and a prism P are arranged in this order. The excitation light emitted by the UV light source 212 is collimated by the collimating lens Lb, and is reflected by the prism P toward the switching mirror 213.

The switching mirror 213 deflects the excitation light toward the aperture stop 215 when located at the second position where the switching mirror 213 is inserted in the optical path of the excitation light. The excitation light reflected by the switching mirror 213 enters the aperture stop 215, where the light amount thereof is adjusted, and then converged, by the condenser lens Lc, on the proximal end surface of the light guide 12b.

As described above, when the switching mirror 213 is located at the first position, only the white light emitted by the white light source 211 is directed to the light guide 12b, and when the switching mirror 213 is located at the second position, only the excitation light emitted by the UV light source 212 is directed to the light guide 12b.

Next, the processor 22 will be described. The processor 22 includes a CPU 221 and a timing generator 222. The CPU 221 is connected with the light source switching mechanism 214, the aperture stop controller 216, the timing generator 222 and the input device 4. The timing generator 222 generates various reference signals for operations executed by the processor 22 and by the OCT unit 23.

The CPU 221 is capable of locating the switching mirror 213 at either the first position or the second position by controlling the light source switching mechanism 214. Specifically, on an operation unit (not shown) of the endoscope 1, a switch for selecting the normal light observation and fluorescent light observation. The CPU 221 detects a status of the selection switch, and controls the light source switching mechanism 214 in accordance with the status of the selection switch. Then, the light source switching mechanism 214 locates the switching mirror 213 at the first position or the second position. That is, when the normal light image is selected, the switching mirror 213 is located at the first position, and when the fluorescent light image is selected, the switching mirror 213 is located at the second position. Further, the CPU 221 controls the aperture stop controller 216, in accordance with a signal from the RGB memory 224, to adjust the aperture size of the aperture stop 215.

The CPU 221 controls operations of the processor 22 and the OCT 23 through the timing generator 222.

The CPU 221 further includes a pre-processing circuit 223 connected to the CCD 14 via the signal line 14a, the RGB memory 224, a video signal processing circuit 225, and a video capture 226 connected to the monitor 3.

The preprocessing circuit 223 processes the video signal output by the CCD 14, converts the video signal (analog signal) into a digital video signal, and stores the digital video signal in the RGB memory 224 as image data.

The video signal processing circuit 225 reads the image data stored in the RGB memory 224 at a predetermined timing and processes the same to generate a video signal, which is transmitted to the video capture 226, and then the image is displayed on the monitor 3.

The processor 22 includes an OCT preprocessing circuit 227 connected to the OCT unit 23, an OCT memory 228 and an OCT video signal processing circuit 229.

The OCT preprocessing circuit 227 processes the signal transmitted from the OCT unit 23, converts the signal (analog) into a digital signal, and stores the same in the OCT memory 228. The OCT video signal processing circuit 229 reads the data stored in the OCT memory 228 at a predetermined timing, and processes the same to generate a video signal, which is transmitted to the video capture 226. The video capture 226 then displays an image on the monitor 3 in accordance with the transmitted video signal.

The OCT unit 23 will be described hereinafter.

Figure 4:
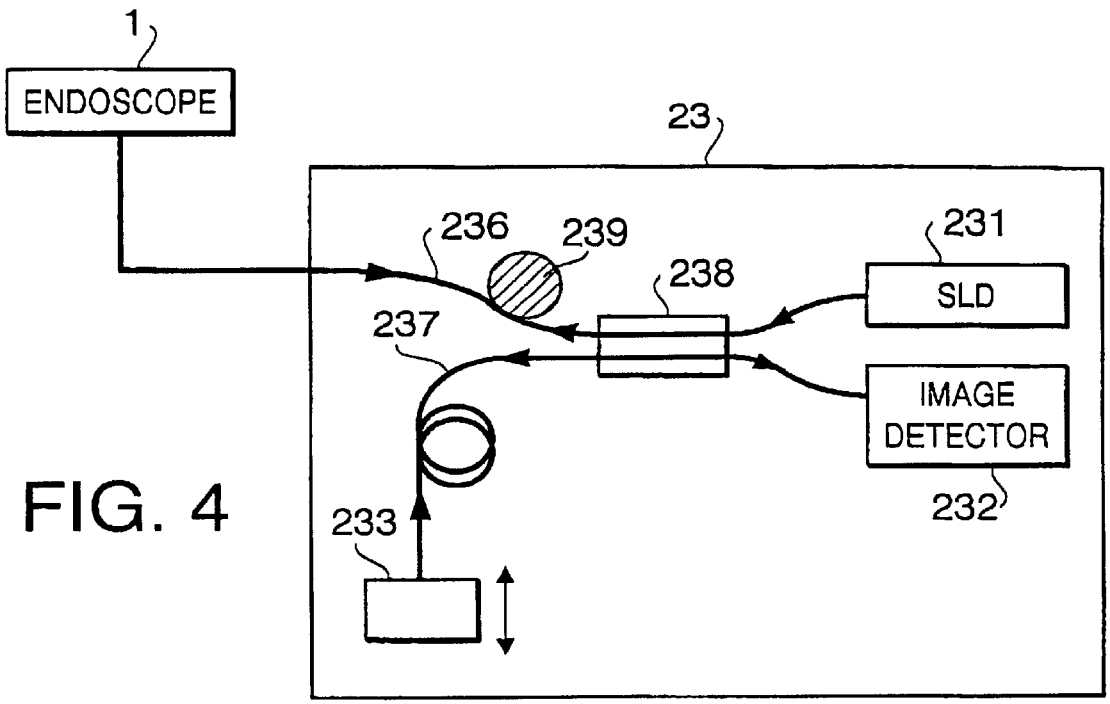

FIG. 4 shows an optical path of the OCT unit 23. The OCT unit 23 is for capturing tomogram beneath the paries of the human cavity with use of the OCT (Optical Coherence Tomogaphy) technique. The OCT unit 23 includes an SLD (superluminescent diode) 231, a photo detector 232, a reference mirror 233, a mirror driving mechanism 234 and a scanning control circuit 235.

The SLD 231 is a light source which emits a low-coherent light beam within a near-infrared region. A coherence length of the light beam emitted by the SLD 231 is very small, and is of the order of 10 $\mu$m to 1000 $\mu$m. The photo detector 232 is, for example, composed of a photo diode. The photo detector 232 is connected to the preprocessing circuit 227 of the preprocessor 22 (see FIG. 1).

The mirror driving mechanism 234 is for moving the reference mirror 233 at a relatively high speed, and is connected to the timing generator 222. The scanning control circuit 235 is connected to the rotating unit 15b of the OCT scanning unit 15, and is also connected to the timing generator 222.

Further, the OCT unit 23 includes a first optical fiber 236 and a second optical fiber 237, a coupler 238 and a piezo modulating element 239. Both the first and second optical fiber 236 and 237 function as single mode optical fibers.

As shown in FIG. 4, the first optical fiber 236 is arranged such that the proximal end surface thereof faces the SLD 231, and the distal end surface thereof faces the scanning prism 15a (see FIG. 2). The second optical fiber 237 is arranged such that the proximal end surface thereof faces the photo detector 232, and that the distal end surface faces the reference mirror 233 (see FIG. 1). The reference mirror 233 can be moved reciprocally in a direction of an axis of the optical fiber 237 (i.e., in a direction perpendicular to the distal end surface of the optical fiber 237), by the mirror driving mechanism 234.

The optical fibers 236 and 237 are optically connected with an optical fiber coupler 238. An optical length of the first optical fiber from the distal end to the optical coupler 238 is the same as that of the second optical fiber 237. Further, a predetermined portion of the first optical fiber 236, i.e., a portion between the coupler 238 and the distal end thereof, is wound around the piezo modulating device 239, which has a cylindrical shape. As the piezo modulating element 239 repeats expansion/reduction in its radial direction at a high speed, a frequency and a phase of the light beam proceeding in the first optical fiber 236 change.

It should be noted that the SLD 231, photo detector 232, reference mirror 233, first and second optical fibers 236 and 237, coupler 238, which is arranged as above, constitute a Michelson interferometer.

When the scanning window S of the insertion tube 11 faces an object to be observed, the OCT unit 23 can capture a tomogram of the objective portion (i.e., paries of body cavity). The principle of capturing the tomogram will be described hereinafter.

The low-coherent light beam emitted by the SLD 231 is incident on the first optical fiber 236, divided into two beams by the coupler 238, and then the two beams proceed, in the first optical fiber 236 and the second optical fiber 237, respectively, towards their distal ends. The light beam proceeding in the first optical fiber 236 is deflected by the scanning prism 15a of the OCT scanning unit 15 in the endoscope 1 (see FIG. 2), and emitted from the scanning window S as a scanning beam. When the scanning window S faces the paries of the human cavity, the scanning beam emitted from the scanning window S is reflected by biotissues located at various depths. The reflected beams enter the endoscope 1 through the scanning window S, then enter the first optical fiber 236 via the scanning prism 15a, and then proceed toward the coupler 238 as detecting light beams.

The other beam divided by the coupler 238 and incident on the second optical fiber 237 is emitted from the distal end thereof, and then, is reflected by the reference mirror 233. The beam reflected by the reference mirror 233 enters the second optical fiber 237 again, and proceeds toward the coupler 238 as a reference light beam.

The detecting light beam in the first optical fiber 236 and the reference light beam in the second optical fiber 237 interfere in the coupler 238. It should be noted that the detecting light beams include beams reflected by layers of biotissues consisting of the body paries, and therefore reach the coupler 238 within a certain range of time. That is, the light beam reflected by the superficial tissue layer reaches the coupler 238 earlier than the light beams reflected by layers at deeper levels.

On the other hand, the reference beam is a beam reflected by the reference mirror 233, thus it is incident on the coupler 238 within a relatively small range of time.

Only part of detecting light beams interfere with the reference light beam. That is, the reference beam interferes with only the part of detecting light beams which proceed along an optical path whose length is substantially the same as that of the optical path from the coupler 238 to the reference mirror 233 via the second optical fiber 237. In other words, a part of detecting light beams reflected by a layer at certain depth under the paries interferes with the reference light beam.

The light beams interfered at the coupler 238 (the interfered light) proceed inside the second optical fiber 237 toward its proximal end, and is detected by the photo detector 232. When the mirror driving mechanism 234 changes the location of the reference mirror 233, the optical path length of the reference beam changes, and therefore, the depth of the layer subject to detection (i.e., interference) changes.

Since the intensity of the light reflected by the biotissues varies depending on the condition of the biotissues, the tomography is obtained based on the intensity distribution of the reflection light from the surface or layers of the paries at a certain depth thereof.

As described above. the photo detector 232 outputs a certain signal in response to the interfered light, while it outputs low-level noise in response to the non-interfered light.

If a signal-to-noise ratio is low, extraction of the signal cannot be performed at a high accuracy. Therefore, in order to improve the signal-to-noise ratio, an optical heterodyne detecting method is employed. Specifically, the frequency and phase of the light guided by the first optical fiber 236 are modulated by the piezo modulating element 239. Then, the phase and frequencies of the detecting light and the reference light shift slightly, and a beat is generated within the interfered light. Accordingly, when the photo detector 232 receives the interfered light carrying the beat, a beat signal is output from the photo detector 232.

The OCT preprocessing circuit 227 is capable of extracting the signal component at high accuracy by demodulating the beat signal output by the photo detector 232.

Next, the operation of the endoscope system 1000 configured as above will be described.

When the operator powers ON the external device 2, the white light source 211 and the UV light source 212 are turned ON. The switching mirror 213 is located at its initial position (i.e., the normal light observation position: the first position), and therefore, only the white light emitted by the white light source 211 is incident on the light guide 12b. The light (i.e., white light) is guided by the light guide 12b, and emitted from the illumination lens 12a.

When the operator inserts the insertion tube 11 of the endoscope 1 in the human cavity of the patient, and objective lens 13a of the objective optical system 13 and the scanning window S face the paries to be observed, the light emitted from the illumination lens 12a illuminates the paries.

Then, an image of the paries is formed on the image receiving surface of the CCD 14 by the objective optical system 13. The CCD 14 outputs a color image signal corresponding to the received optical image to the preprocessing circuit 223. The preprocessing circuit 223 receives the image signal, amplifies and applies some processing to the received signal, and then converts the same to the digital image signal, which is stored In the RGB memory as image data. The video signal processing circuit 225 reads the image data stored in the RGB memory 224 at a predetermined timing, processes the same to produce a video signal, and transmits the video signal to the video capture 226. Accordingly, the video capture 226 displays an image on the monitor 3 as a normal light image. The operator can observe the surface of the paries of the patient by observing the image displayed on the monitor 3.

If the operator changes the operation status of the switch of the operation unit to select the fluorescent light image, the CPU 221 controls the light source switching mechanism 214 to locate the switching mirror 213 at the fluorescent image observing position (i.e., the second position). Then, the white light emitted by the white light source 211 is shielded by the switching mirror 213, and the excitation light emitted by the UV light source 212 is directed to the light guide 12b. The light incident on the light guide 12b is guided thereby, and then emitted toward the paries through the illumination lens 12a of the endoscope 1.

The tissues of the paries emit fluorescent light when illuminated by the excitation light. It is known that the diseased tissues emit the fluorescent light which is weaker than that emitted by healthy tissues.

The fluorescent light emitted by the biotissues are incident on the objective optical system 13 together with the reflected excitation light. The excitation light is shielded by a cut off filter provided in the objective optical system 13, and only the fluorescent light passes through the objective optical system 13. The fluorescent light is converged on a plane that is located in the vicinity of the image receiving surface of the CCD 14. That is, an image (a fluorescent light image) is formed on the image receiving surface of the CCD 14.

The CCD 14 outputs an image signal corresponding to the fluorescent light image formed thereon to the preprocessing circuit 223. The preprocessing circuit 223 receives the image signal, applies predetermined procedures such as amplifying, and converts the image signal into digital image signal, which is stored in the RGB memory 224 as digital image data. The video signal processing circuit 225 reads out thus stored image data at a predetermined timing, processes the same to generate a video signal. The video signal Is transmitted to the video capture 226, which displays an image on the monitor 3 as the fluorescent light image.

The operator can observe the fluorescent light image of the tissues through the monitor 3. If there are portions which are darker than the other portions in the fluorescent image, the operator can recognize that the darker portion might include cancers and/or tumors.

As above, when portions which might be diseased are identified, a tomogram can be obtained. That is, when the operator operates the operation unit to select the tomography, the CPU 221 causes the OCT 23 such that the low-coherent light is emitted from the SLD 231, and controls the mirror driving mechanism 234 and the scanning control circuit 235 to start capturing tomogram. At the same time, the CPU 221 controls the timing generator 222 to transmit clock signals to RGB memory 224 and the OCT memory 228, respectively. The RGB memory 224 and the OCT memory 228 transmit, in accordance with the clock signals, signals to the video signal processing circuit 225 and the OCT video signal processing circuit 229, respectively, at predetermined timing.

The scanning control circuit 235 controls the rotating unit 15b of the OCT scanning unit 15 so that the scanning prism 15a reciprocally rotates within a predetermined angular range about the axis of the optical fiber 236. The light emitted from the tip end of the optical fiber 236 is emerged from the scanning window S, and repeatedly scans a predetermined area along a direction perpendicular to the axis of the insertion tube 11. That is, on the surface of the paries, a linearly extending scanning line is formed. The scanning line virtually includes a plurality of discrete scanning points, and the light emitted from the scanning window S sequentially scans the scanning points.

Simultaneously with the above scanning, the mirror driving mechanism 234 reciprocally moves the reference mirror 233 in a direction parallel with the axis of the optical fiber 237. It should be noted that the mirror driving mechanism 234 and the scanning control circuit 235 operate synchronously with the clock signals transmitted from the timing generator 222. That is, while the light beam is considered to impinge on one of the scanning points, the reference mirror 233 reciprocates once. Therefore, when the light beam emitted from the scanning window S scans the scanning line once, scanning is performed with respect to a predetermined depth range from the surface of the paries to a certain depth (e.g., 2 mm) therefrom.

Specifically, the scanning in the depth direction is performed from a position closer to the scanning window S with respect to the surface of the paries to a position deeper than the predetermined depth. During this scanning, the OCT preprocessing circuit 227 continuously monitors the output of the photo detector 232. The OCT preprocessing circuit 227 does not detect a signal when a scanning position in the depth direction has not yet reached the surface of the paries. When the scanning position in the depth direction has reached the surface of the paries, the OCT preprocessing circuit 227 detects a signal, and calibration is performed such that the scanning position at which the signal is firstly detected is regarded as the surface of the paries. That is, the OCT preprocessing circuit 227 recognizes the depth at which the signal is detected firstly as the surface of the paries (i.e., the depth is zero), and signals obtained within a range starting from the position to the predetermined depth (e.g., 2 mm) are subject to measurement.

Then, the OCT preprocessing circuit 227 performs decoding, amplifying and analog-to-digital conversion with respect to the signals determined to be subject to measurement. The data obtained after the above processing is stored in the OCT memory 228. The OCT video signal processing circuit 229 processes the data stored in the OCT memory 228 at a predetermined timing to generate a video signal, which is transmitted to the video capture 226. The video capture 226 then displays an image corresponding to the transmitted video signal on the monitor 3. The tomogram within a range from the surface of the paries to the predetermined depth is displayed on the monitor 3.

Figure 5:
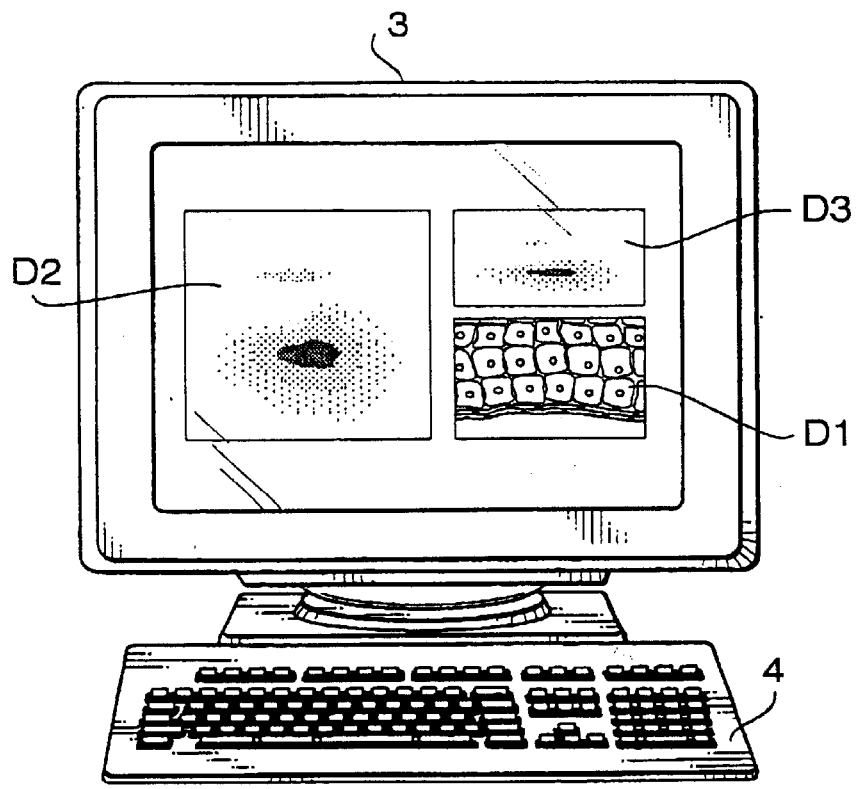
FIG. 5 shows an example of images displayed on a monitor.
Figure 6:
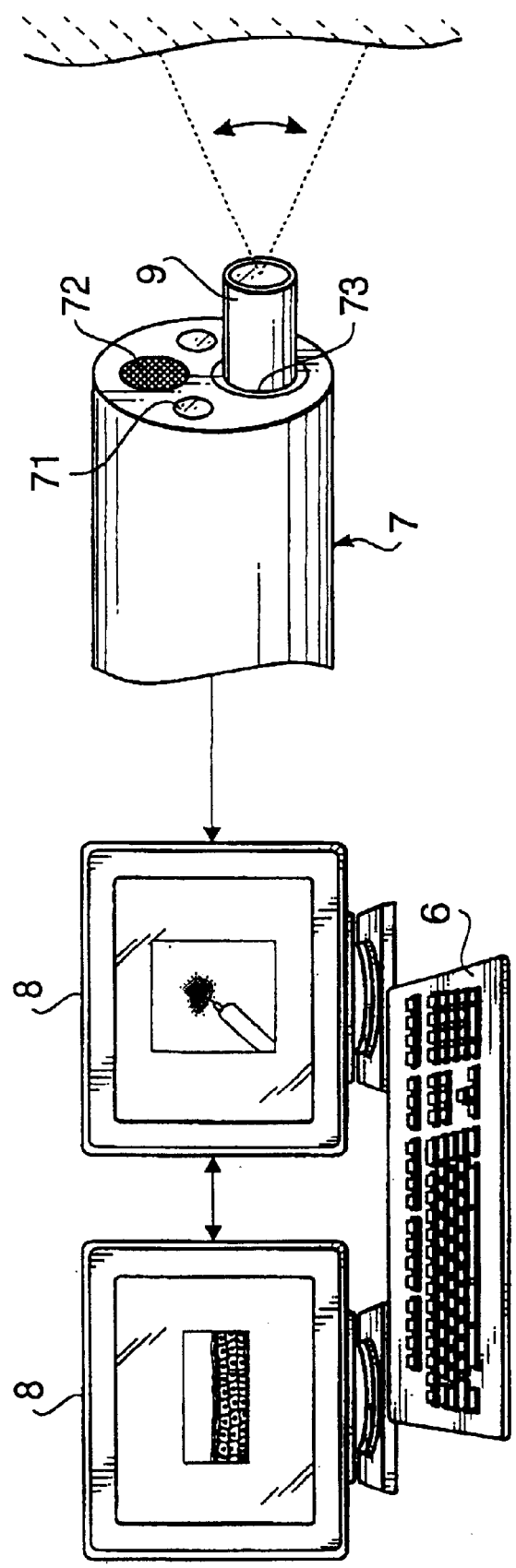
FIG. 6 shows an example of conventional endoscope system capable of capturing an OCT image.

It should be noted that the video capture 226 is capable of displaying the tomogram image together with the normal light image or the fluorescent light image. FIG. 5 shows an example of a screen image of the monitor 3. That is, the RGB memory 224 and the OCT memory 228 receive the clock signals from the timing generator in accordance with command by the CPU 21, and sends signals to the video signal processing circuit 225 and the OCT video signal processing circuit at predetermined timings, respectively.

The video capture 226 displays images corresponding to signals transmitted from the video signal processing circuit 255 and the OCT signal processing circuit 229 in respective areas on a screen of the image.

In FIG. 5, the screen of the monitor 3 is divided into three displaying areas on which a tomogram image D1, a normal light image D2 and a fluorescent light image D3 are displayed, respectively. In this embodiment, one of the normal light image D2 and the fluorescent light image D3 is displayed as an animating image, and the other is displayed as a still image.

It should be noted that the flatter portion 11b of the insertion tube 11 and the scanning window S are located outside the viewing angle of the objective optical system 13. Therefore, in the normal light image D2 and the fluorescent light image D3, such parts of the endoscope 1 will not be included. Accordingly, the operator can observe the entire range of the viewing angle of the objective optical system 13.

Further, the scanning window S is arranged so as to face the central portion of the field of view of the objective optical system 13. Therefore, the tomogram D1 corresponds to the central area of the normal light image D2 and the fluorescent light image D3. Accordingly, the operator can recognize the positional relationship between the tomogram with respect to the normal and fluorescent light images D2 and D3.

With this configuration, the operator can observe a tomogram only by directing the scanning window S to a portion which might be diseased in view of the observation of the normal light image D2 and/or fluorescent light image D3. That is, the operator can observe the tomogram D1 with referring to the normal light image D2 and/or fluorescent light image D3. Therefore, only by using the endoscope 1, the early cancer or a small tumor can be found easily.

The optical path of the objective optical system 13 is independent of the optical path of the OCT unit 23, and the half mirror, dichroic mirror or the like is not provided within the optical path of the objective optical system 13. Therefore, with the endoscope described above, a bright and clear normal light image D2 and fluorescent light image D3 can be obtained.

Further, since the accurate and quick diagnosis becomes available, the operator can perform the necessary treatment immediately. That is, by inserting a treatment instrument such as forceps or laser treatment instrument through the treatment-inserting channel and necessary treatment can be completed on the moment.

In the above-described embodiment, the reference mirror is reciprocated once when the scanning beam impinges on each scanning point to obtain the tomogram image. In other words, for each scanning point, a scanning in depth direction is performed. Alternatively, the tomogram image can be obtained by locating the reference mirror at a plurality of positions, and the scanning along the scanning line is repeated for respective positions of the reference mirror. In this method, for each positions in the depth direction, the scanning along the scanning line is performed.

The present disclosure relates to the subject matters contained in Japanese Patent Applications Nos. HEI 11-189110 and HEI 11-189111, both filed on Jul. 2, 1999, which are expressly incorporated herein by reference in their entireties.

What is claimed is:

1. An endoscope system, comprising:
   an illuminating optical system that emits at least one of visible light and excitation light for illuminating an object to be observed, the excitation light causing biotissues to fluoresce;
   an objective optical system that converges light from the object to form an optical image of the object;
   an insertion tube comprising:
   a) a cylindrical portion;
   b) a flatter portion formed at a tip of said cylindrical portion;
   c) an inclined surface configured to connect respective side surfaces of said cylindrical portion and said flatter portion;
   d) a scanning window on a surface of said flatter portion, said scanning window located out of a field of view of said objective optical system, said scanning window configured to face an object that is located within the field of view of said objective optical system;
   an image capturing system that captures the optical image formed by said objective optical system;
   a first light guide;
   a second light guide;
   a coupler, said first and second light guides being optically coupled by said coupler;
   a low-coherent light source arranged on a proximal end side of one of said first and second light guides, a low-coherent light beam emitted by said low-coherent light source being incident on said one of said first and second light guides;
   a scanning unit configured to cause the low-coherent light beam emerged from a tip of said first light guide, to scan on the object, the low-coherent light reflected by the object being directed to said first light guide by said scanning unit as detecting light, said scanning unit further configured to emit said low-coherent light beam through said scanning window;
   a mirror that reflects the low-coherent light beam emerged from a tip of said second light guide so as to impinge on the tip of said second light guide as reference light;
   an optical path length adjusting system that changes a length of an optical path from said coupler to the object via said first light guide relative to a length of an optical path from said coupler to said mirror via said second light guide;
   a detector arranged on a proximal end side of the other of said first and second light guides, said detector detecting interference fringe generated by interference between the detecting light and the reference light and outputs an electrical signal; and
   a signal processing system that captures a tomogram of the object based on the signal that is output by said detector when the optical path length adjusting system and said scanning unit operate;
   wherein:
   said illuminating optical system comprises an illuminating lens that is fixed on said inclined surface and is configured to emit light toward the object, and
   said objective optical system includes an objective lens that is fixed on said inclined surface and is configured to receive the light from the object.

2. The endoscope system according to claim 1, said optical path length adjusting system varies the length of the optical path from said coupler to the object via said first light guide relative to the length of the optical path from said coupler to said mirror via said second light guide by moving said mirror in a direction parallel to the central axis of the tip of said second light guide.

3. The endoscope system according to claim 1, wherein said signal processing system forms a tomogram of the object based on the signal output by said detector when said optical path length adjusting system periodically varies the length of the optical path from said coupler to the object via said first light guide relative to the length of the optical path from said coupler to said mirror via said second light guide, and when said scanning unit operates.

4. The endoscope system according to claim 1, wherein said signal processing system forms a tomogram when said optical path length adjusting system sequentially varies the length of the optical path from said coupler to the object via said first light guide relative to the length of the optical path from said coupler to said mirror via said second light guide for each scanning position.

5. The endoscope system according to claim 1, further comprising:
   a visible light source;
   an excitation light source;
   a light source switching system that selectively introduces the light emitted by said visible light source and said excitation light source to said illuminating optical system,
   wherein said objective optical system forms a normal light image of the object when the visible light is introduced to said illuminating optical system, and
   wherein said objective optical system forms a fluorescent light image of the object when the excitation light is introduced to said illuminating optical system.

6. The endoscope system according to claim 1, wherein said low-coherent light source includes a super high intensity light emitting diode.

7. The endoscope system according to claim 1, further comprising a display system for displaying an image of the surface of the object captured by said image capturing system and the tomogram of the object obtained by said signal processing system.

8. The endoscope system according to claim 1, said optical path length adjusting system varies the length of the optical path from said coupler to the object via said first light guide relative to the length of the optical path from said coupler to said mirror via said second light guide by moving said mirror in a direction parallel to the central axis of the tip of said second light guide.

9. The endoscope system according to claim 1, further comprising:
   a visible light source;
   an excitation light source;
   a light source switching system that selectively introduces the light emitted by said visible light source and said excitation light source to said illuminating optical system,
   wherein said objective optical system forms a normal light image of the object when the visible light is introduced to said illuminating optical system, and wherein said objective optical system forms a fluorescent light image of the object when the excitation light is introduced to said illuminating optical system.

10. The endoscope system according to claim 1, further comprising a display system for displaying an image of the surface of the object captured by said image capturing system and the tomogram of the object obtained by said signal processing system.

* * * * *